US012239577B2

(12) United States Patent
Steinlechner et al.

(10) Patent No.: US 12,239,577 B2
(45) Date of Patent: Mar. 4, 2025

(54) OPHTHALMOLOGICAL DEVICE FOR TREATMENT OF A CORNEA

(71) Applicant: Ziemer Ophthalmic Systems AG, Port (CH)

(72) Inventors: Michael Steinlechner, Zurich (CH); Christian Rathjen, Bremen (DE); Werner Bernau, Köniz (CH)

(73) Assignee: Ziemer Ophthalmic Systems AG, Port (CH)

( * ) Notice: Subject to any disclaimer, the term of this patent is extended or adjusted under 35 U.S.C. 154(b) by 612 days.

(21) Appl. No.: 17/558,929

(22) Filed: Dec. 22, 2021

(65) Prior Publication Data

US 2022/0192882 A1 Jun. 23, 2022

Related U.S. Application Data

(63) Continuation-in-part of application No. 17/130,616, filed on Dec. 22, 2020, now Pat. No. 11,717,442.

(30) Foreign Application Priority Data

Apr. 19, 2021 (CH) .......................................... 407/21
May 28, 2021 (CH) .......................................... 616/21

(51) Int. Cl.
*A61F 9/008* (2006.01)

(52) U.S. Cl.
CPC ...................... *A61F 9/00802* (2013.01); *A61F 2009/00851* (2013.01); *A61F 2009/00872* (2013.01)

(58) Field of Classification Search
CPC ........ A61F 9/00802; A61F 2009/00851; A61F 2009/00872
See application file for complete search history.

(56) References Cited

U.S. PATENT DOCUMENTS

| 7,621,637 | B2 | 11/2009 | Rathjen et al. |
| 8,685,007 | B2 | 4/2014 | Vogelsang et al. |
| 10,575,989 | B2 | 3/2020 | Dishler et al. |

(Continued)

FOREIGN PATENT DOCUMENTS

| DE | 102005014760 A1 | 10/2006 |
| DE | 102016218564 A1 | 3/2017 |

(Continued)

OTHER PUBLICATIONS

Oct. 6, 2021—(CH) Search Report—App 6162021.

*Primary Examiner* — Gary Jackson
*Assistant Examiner* — Sebastian X Lukjan
(74) *Attorney, Agent, or Firm* — Banner & Witcoff, Ltd.

(57) ABSTRACT

An ophthalmological device for treatment of a cornea comprises a laser source, a focusing optical module, a scanner system, and an electronic circuit. The electronic circuit is configured to control the scanner system to move the focal spot of the pulsed laser beam to generate a void volume inside the cornea by ablating cornea tissue with partially overlapping focal spots, whereby two or more focal spots partially overlap in direction of each of three dimensions of the void volume, and to move the focal spot inside the cornea to cut in the cornea a venting channel which connects fluidically the void volume to an escape area and enables venting of gas from the void volume through the venting channel to the escape area.

20 Claims, 6 Drawing Sheets

(56) References Cited

U.S. PATENT DOCUMENTS

| | | | |
|---|---|---|---|
| 11,717,442 B2* | 8/2023 | Steinlechner | A61F 9/00827 606/4 |
| 2007/0010804 A1 | 1/2007 | Rathjen et al. | |
| 2010/0331831 A1 | 12/2010 | Bischoff et al. | |
| 2011/0184394 A1 | 7/2011 | Donitzky et al. | |
| 2013/0281992 A1 | 10/2013 | Seiler et al. | |
| 2016/0089270 A1 | 3/2016 | Fu | |
| 2017/0128261 A1* | 5/2017 | Deisinger | A61F 9/00825 |
| 2017/0367883 A1* | 12/2017 | Malek Tabrizi | A61F 9/0084 |
| 2019/0015250 A1 | 1/2019 | Rathjen | |
| 2019/0015251 A1 | 1/2019 | Rathjen | |
| 2019/0015253 A1 | 1/2019 | Rathjen | |
| 2019/0175400 A1* | 6/2019 | Loerner | A61F 9/00825 |
| 2020/0069470 A1* | 3/2020 | Fu | A61F 9/00827 |
| 2020/0206033 A1 | 7/2020 | Dishler et al. | |

FOREIGN PATENT DOCUMENTS

| | | |
|---|---|---|
| EP | 1731120 A1 | 12/2006 |
| EP | 2211804 | 8/2010 |
| WO | 2004052253 A1 | 6/2004 |
| WO | 2011088848 A1 | 7/2011 |
| WO | 2014135218 A1 | 9/2014 |

\* cited by examiner

OPHTHALMOLOGICAL DEVICE FOR TREATMENT OF A CORNEA

CROSS-REFERENCE TO RELATED APPLICATIONS

The present application is a continuation-in-part of U.S. application Ser. No. 17/130,616, filed Dec. 22, 2020, which is incorporated by reference in its entirety. The present application also claims priority to and the benefit of Switzerland Patent Application 00407/21, filed Apr. 19, 2021, and Switzerland Patent Application 00616/21, filed May 28, 2021, which are incorporated by reference in their entirety herein.

FIELD OF THE DISCLOSURE

The present disclosure relates to an ophthalmological device for treatment of a cornea. In particular, the present disclosure relates to an ophthalmological device comprising a laser source for generating a pulsed laser beam, a focusing optical module for converging the pulsed laser beam onto a focal spot in the cornea, and a scanner system for moving the focal spot to target locations in the cornea for generating a void volume inside the cornea.

BACKGROUND OF THE DISCLOSURE

For the purposes of working on eye tissue by means of a laser beam, a work region is scanned by laser pulses by virtue of the pulsed laser beam being deflected in one or more scan directions by means of suitable scanner systems. In general, movable mirrors are used to deflect the light beams and/or the laser pulses, for example femtosecond laser pulses, said movable mirrors being pivotable about one or two scan axes, for example by way of galvano scanners, piezo scanners, polygon scanners, or resonance scanners.

U.S. Pat. No. 7,621,637 describes an apparatus for working on eye tissue, said apparatus having a base station with a laser source for producing laser pulses and a scanner, arranged in the base station, with movable deflection mirrors for deflecting the laser pulses in a scan direction. The deflected laser pulses are transferred via an optical relay system from the base station to an application head, the latter passing over a work region according to a scan pattern by means of a mechanically moved projection optical unit. According to U.S. Pat. No. 7,621,637, in the application head, the deflection in the scan direction, which is much faster in comparison with the mechanical movement, is overlaid onto the mechanical movement of the projection optical unit and consequently onto the scan pattern thereof. A fast scanner system in the base station facilitates a fine movement of the laser pulses (micro-scan), which is overlaid on the scan pattern of the (mechanically) movable projection optical unit that covers a large work region, for example the entire eye.

For treatment of the cornea, pulsed laser radiation is used in corneal surgery to cut and remove conical tissue. Using femtosecond laser pulses to generate cuts inside the cornea produces gas inside the cornea. As this gas produces cloudy areas in the cornea, it may impair the quality of subsequent neighbouring or overlapping cuts and thereby compromise significantly the quality of the cut surface and the intended refractive correction, for example. To alleviate the negative impact of gas produced during the cutting process, WO 2011/088848 and DE102016218564 teach the cutting of venting pockets inside the cornea, which receive and collect the unwanted gas. Nevertheless, when lenticules are cut inside the cornea for refractive correction, these venting pockets may still have a negative impact as the build-up of pressure by the gas inside the venting pockets may be detrimental to the precision of corneal cuts which is absolutely required in case of refractive correction.

For refractive correction of the cornea, a lenticule is created inside the cornea. To achieve the refractive correction, the created lenticule is subsequently removed from the cornea through one or more extraction channels cut in the cornea.

US 2016/0089270 describes a system and a method for cutting lenticules in the eye tissue. According to US 2016/0089270, straight-lined fast scan lines are overlaid to this end on slower work lines that are traced out along meridians of the lenticule.

Theoretically, the exact form, including shape and size, of the lenticule to be removed for refractive correction of the cornea can be determined using standard optical lens formulas, which produce zero thickness at the border (for myopic corrections) or at the center (for hyperopic corrections). However, cutting these shapes directly into the cornea produces unstable lenticules which are hard to manipulate by the surgeon and, owing to the extreme thinness of their central or peripheral areas, have a propensity of at least partially ripping during the extraction. Moreover, the corneal stroma bed is structured in lamellæ (collagen layers) with a thickness of approximately 2 µm. Cutting structures, which are close to this scale thus often produces frayed edges. The partial tears and frayed edges make it difficult for a surgeon to judge whether the lenticule was indeed extracted successfully in its entirety from the patient's eye.

EP 2211804 describes an apparatus for operatively correcting myopia or hyperopia in an eye by emitting laser radiation into the cornea to cut a lenticule, which is removed from the cornea for the desired refractive correction. To avoid the aforementioned problems of partial tears and frayed edges, EP 2211804 teaches to cut the lenticule with a minimum thickness in the range of 5 µm to 50 µm at the edge of the lenticule for correction of myopia and in the region of the axis of vision for correction of hyperopia. Nevertheless, increasing the thickness of the lenticule goes hand in hand with an undesirable enlargement of the lenticular cornea tissue, which is removed, from the cornea. While the enlargement of the lenticular improves its structural stability, it unnecessarily weakens the cornea itself and partly counteracts the minimally invasive nature of the lenticule extraction procedure.

SUMMARY OF THE DISCLOSURE

It is an object of the present disclosure to propose an ophthalmological device for treatment of a cornea of an eye by generating a void volume inside the cornea using a pulsed laser beam, which device does not have at least some of the disadvantages of the prior art. Particularly, it is an object of the present disclosure to propose an ophthalmological device for treatment of a cornea by generating a void volume inside the cornea using a pulsed laser beam, which device reduces the detrimental impacts of torn tissue parts inside the cornea and gas produced when applying the pulsed laser beam inside the cornea.

According to the present disclosure, these objects are achieved by the features of the independent claims. Moreover, further advantageous embodiments emerge from the dependent claims and the description.

An ophthalmological device for treatment of a cornea of an eye, by generating a void volume inside the cornea, comprises: a laser source configured to generate a pulsed laser beam; a focusing optical module configured to make the pulsed laser beam converge onto a focal spot in the cornea; a scanner system configured to move the focal spot to target locations in the cornea; and an electronic circuit configured to control the scanner system.

According to the present disclosure, the above-mentioned objects are particularly achieved in that the electronic circuit is configured to control the scanner system to move the focal spot inside the cornea to generate the void volume by ablating cornea tissue inside the cornea with partially overlapping focal spots, whereby two or more focal spots partially overlap in direction of each of three dimensions of the void volume, and to move the focal spot inside the cornea to cut in the cornea a venting channel, the venting channel connecting fluidically the void volume to an escape area to enable venting of gas, produced by generating the void volume inside the cornea, from the void volume through the venting channel to the escape area. Generating the void volume by ablating cornea tissue inside the cornea with partially overlapping focal spots, whereby two or more focal spots partially overlap in direction of each of three dimensions of the void volume, means that each of the focal spots partially overlaps in direction of each of the three dimensions of the void volume with at least one other focal spot.

In an embodiment, the electronic circuit is configured to control the scanner system to move the focal spot inside the cornea to cut an opening incision in an exterior surface of the cornea, and to cut the venting channel such that the venting channel connects fluidically the void volume to the opening incision to enable venting of the gas from the void volume through the opening incision to an escape area exterior to the cornea.

In an embodiment, the ophthalmological device further comprises a patient interface, the patient interface comprising a contact body, whereby in a state where the patient interface is fixed to the cornea the contact body is in contact with the exterior surface of the cornea in an applanation zone, and the electronic circuit is configured to control the scanner system to move the focal spot inside the cornea to cut in the cornea the venting channel with the opening incision located in a peripheral area of the exterior surface of the cornea outside the applanation zone.

In an embodiment, the patient interface further comprises one or more suction elements configured to fix the contact body to the cornea, and in the state where the patient interface is fixed to the cornea the one or more suction elements and the contact body form an external venting chamber with the peripheral area of the exterior surface of the cornea outside the applanation zone; and the electronic circuit is configured to control the scanner system to move the focal spot inside the cornea to cut in the cornea the venting channel with the opening incision inside the external venting chamber.

In an embodiment, the one or more suction elements are configured to apply a partial vacuum to the venting chamber and thereby further enable the venting of the gas.

In an embodiment, the electronic circuit is configured to control the scanner system to move the focal spot inside the cornea to ablate the cornea tissue inside the cornea to generate the void volume in shape of a ring and/or a lenticule.

In an embodiment, the electronic circuit is configured to control the scanner system to move the focal spot inside the cornea to ablate the cornea tissue inside the cornea to generate the void volume such that the void volume has a rounded rim.

In an embodiment, the electronic circuit is configured to control the scanner system to move the focal spot inside the cornea to cut a venting pocket inside the cornea, whereby the venting pocket is cut in at least one of the following configurations:

(a) the venting pocket is cut as the escape area, fluidically connected to the void volume by the venting channel, to enable venting of the gas from the void volume through the venting channel to the venting pocket;

(b) the venting pocket is cut as an intermediary escape area, fluidically connected to the void volume by a first part of the venting channel and fluidically connected to an opening incision in an exterior surface of the cornea by a second part of the venting channel, to enable venting of the gas from the void volume through the first part of the venting channel to the venting pocket and from the venting pocket through the second part of the venting channel and through the opening incision to an escape area exterior to the cornea;

(c) the venting pocket is cut as an intermediary escape area, adjacent and fluidically connected to the void volume and fluidically connected to the opening incision in the exterior surface of the cornea by the venting channel, to enable venting of the gas from the void volume to the venting pocket and from the venting pocket through the venting channel and through the opening incision to the escape area exterior to the cornea; or (d) the venting pocket is cut as an intermediary escape area, surrounding the void volume and fluidically connected to the void volume and fluidically connected to the opening incision in the exterior surface of the cornea by the venting channel, to enable venting of the gas from the void volume to the venting pocket and from the venting pocket through the venting channel and through the opening incision to the escape area exterior to the cornea.

In an embodiment, the scanner system comprises a first scanner device configured to move the focal spot with a first scanning speed to target locations along a working line, and a second scanner device configured to move the focal spot with a second scanning speed, comparatively faster than the first scanning speed, to target locations along a scan line which runs through the working line at an angle to the working line; and the electronic circuit is configured to control the first scanner device to move the focal spot to target locations along a spiral shaped working line inside the cornea, and to control the second scanner device to move the focal spot to target locations along the scan line to ablate the cornea issue and generate the void volume.

In an embodiment, the scanner system comprises a divergence modulator configured to modulate a divergence of the pulsed laser beam for adjusting a location of the focal spot along an optical axis of the focusing optical module and tilting the scan line in direction of the optical axis; and the electronic circuit is configured to control the divergence modulator to adjust a tilting angle of the scan line with respect to the shape of an anterior volume surface of the void volume and/or a posterior volume surface of the void volume.

In an embodiment, the scanner system comprises a length modulator configured to modulate a length of the scan line; and the electronic circuit is configured to control the length modulator to adjust the length of the scan line with respect to the shape of an anterior volume surface of the void volume or a posterior volume surface of the void volume.

In an embodiment, the electronic circuit is configured to control the scanner system to move the focal spot along a work line to cut the venting channel and an anterior volume surface of the void volume and/or a posterior volume surface of the void volume in a continuous movement of the focal spot along the work line.

In an embodiment, the ophthalmological device further comprises a measurement system configured to determine positional reference data of the cornea, and the electronic circuit is configured to control the scanner system to move the focal spot inside the cornea to cut the venting channel, using the positional reference data.

In an embodiment, the measurement system comprises a video capturing system and/or an optical coherence tomography system.

In addition to the ophthalmological device for treatment of a cornea of an eye, the present disclosure further relates to a computer program product, particularly, a computer program product comprising a non-transitory computer-readable medium having stored thereon computer program code for controlling a processor of an ophthalmological device for treatment of a cornea of an eye by generating a void volume inside the cornea. The ophthalmological device comprises a laser source configured to generate a pulsed laser beam, a focusing optical module configured to make the pulsed laser beam converge onto a focal spot in the cornea, and a scanner system configured to move the focal spot to target locations in the cornea. The computer program code is configured to control the processor such that the processor directs the scanner system to move the focal spot inside the cornea to generate a void volume inside the cornea, by ablating cornea tissue inside the cornea with partially overlapping focal spots, whereby two or more focal spots partially overlap in direction of each of three dimensions of the void volume, and to move the focal spot inside the cornea to cut in the cornea a venting channel, the venting channel connecting fluidically the void volume to an escape area, to enable venting of gas, produced by generating the void volume inside the cornea, from the void volume through the venting channel to the escape area, whereby the escape area is exterior to the cornea or inside the cornea. Generating the void volume by ablating cornea tissue inside the cornea with partially overlapping focal spots, whereby two or more focal spots partially overlap in direction of each of three dimensions of the void volume, means that each of the focal spots partially overlaps in direction of each of the three dimensions of the void volume with at least one other focal spot.

In an embodiment, the computer program product has further computer program code stored on the computer-readable medium and configured to control the processor such that the processor controls the scanner system to move the focal spot inside the cornea to ablate the cornea tissue inside the cornea to generate the void volume in shape of a ring and/or a lenticule.

In an embodiment, the computer program product has further computer program code stored on the computer-readable medium and configured to control the processor such that the processor controls the scanner system to move the focal spot along a work line to cut the venting channel and an anterior volume surface of the void volume and/or a posterior volume surface of the void volume in a continuous movement of the focal spot along the work line.

BRIEF DESCRIPTION OF THE DRAWINGS

The present disclosure will be explained in more detail, by way of example, with reference to the drawings in which.

DETAILED DESCRIPTION OF THE EMBODIMENTS

Figure 1:
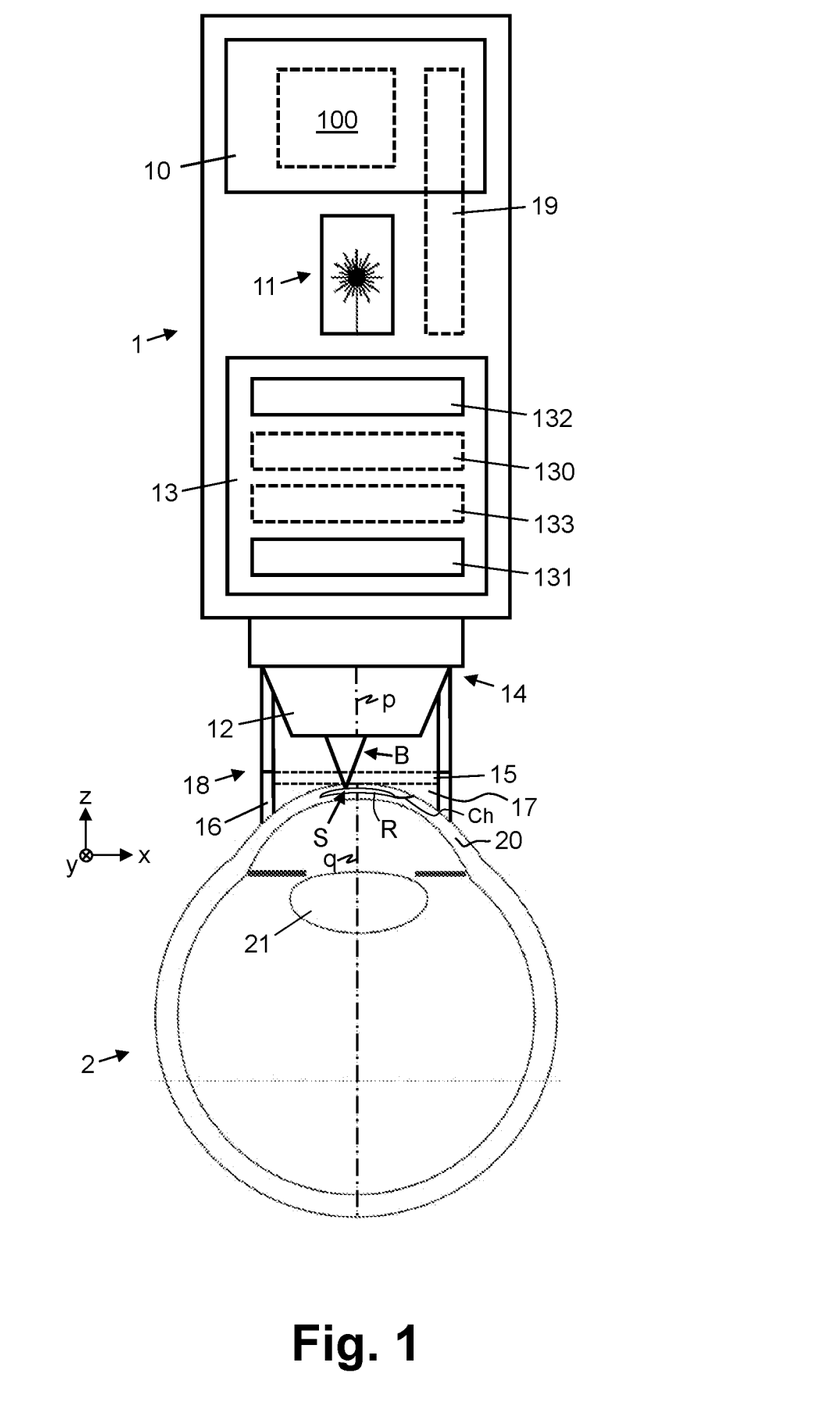
FIG. 1 shows a block diagram that schematically illustrates an ophthalmological device for treatment of a cornea with a pulsed laser beam, said device comprising a focusing optical module for focusing the pulsed laser beam in the cornea, and a scanner system for moving the focal spot to target locations in the cornea.

In FIG. 1, reference numeral 1 relates to an ophthalmological device for treatment of a cornea 20 of an eye 2 by generating a void volume R inside the cornea 20, using a pulsed laser beam B. Specifically, the ophthalmological device 1 is configured to generate the void volume R inside the cornea 20 for refractive correction of the cornea 20 and/or for other purposes, such as for inserting implants into the cornea 20.

As illustrated schematically in FIG. 1, the ophthalmological device 1 comprises a laser source 11 for generating the pulsed laser beam B, a focusing optical module 12 for focusing the pulsed laser beam B in the cornea 20 onto a focal spot S, and a scanner system 13 for moving the focal spot S to target locations in the cornea 20. As explained later in more detail, the scanner system 13 is configured to move the focal spot S to target locations along work lines w and scan lines c in the cornea 20.

The ophthalmological device 1 further comprises an electronic circuit 10 for controlling the laser source 11 and the scanner system 13. The electronic circuit 10 implements a programmable control device and comprises e.g. one or more processors 100 with program and data memory and programmed software modules for controlling the processors 100, and/or other programmable circuits or logic units such as ASICs (application specific integrated circuits).

The laser source 11 comprises a femtosecond laser for producing femtosecond laser pulses, which have pulse widths of typically 10 fs to 1000 fs (1 fs=$10^{-15}$ s). The laser source 11 is arranged in a separate housing or in a housing shared with the focusing optical module 12.

The focusing optical module 12 is configured to focus the pulsed laser beam B or the laser pulses, respectively, in the cornea 20 onto a focal spot S, i.e. for making the pulsed laser beam B converge to a focus or focal spot in the cornea 20. The focusing optical module 12 comprises one or more optical lenses. In an embodiment, the focusing optical module 12 comprises a focus adjustment device for setting the focal depth of the focal spot S, for example one or more movable lenses, in the focusing optical module 12 or upstream of the focusing optical module 12, or a drive for moving the entire focusing optical module 12 along the projection axis p (z-axis). By way of example, the focusing optical module 12 is installed in an application head 14, which can be placed onto the eye 2.

Figure 12:
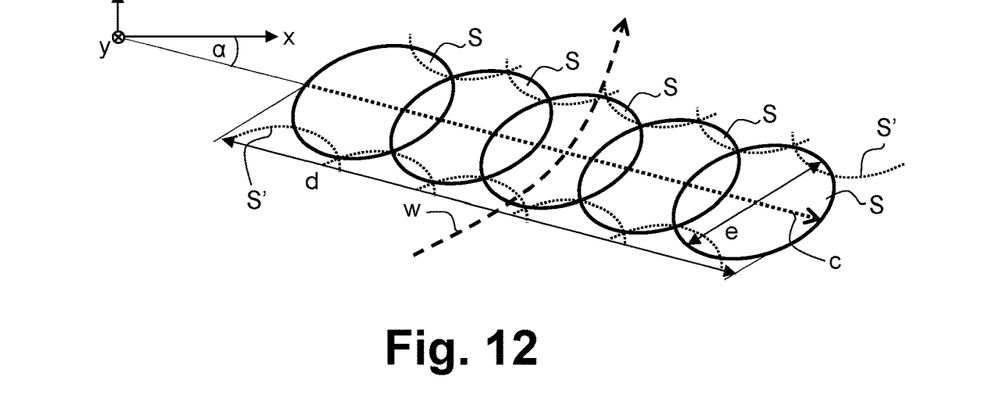
FIG. 12 shows a schematic top view of a scan line, running at an angle through a working line, with a series of partially overlapping focal spots moved by the scanner system along the scan line.
Figure 13:
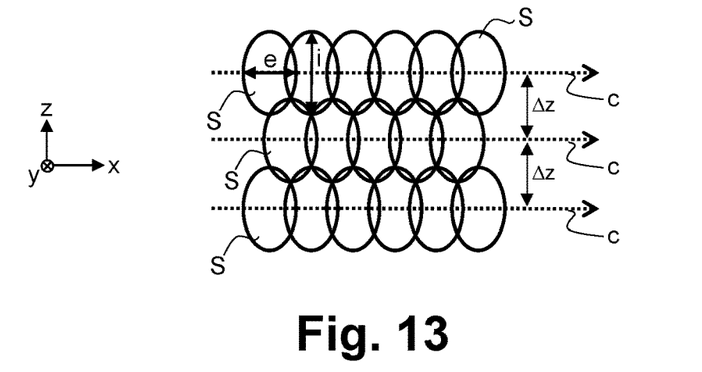
FIG. 13 shows a schematic cross-sectional view of superposed scan lines with focal spots moved by the scanner system along the scan line, whereby the focal spots partial overlap along the scan line and across the superposed scan lines.
Figure 14:
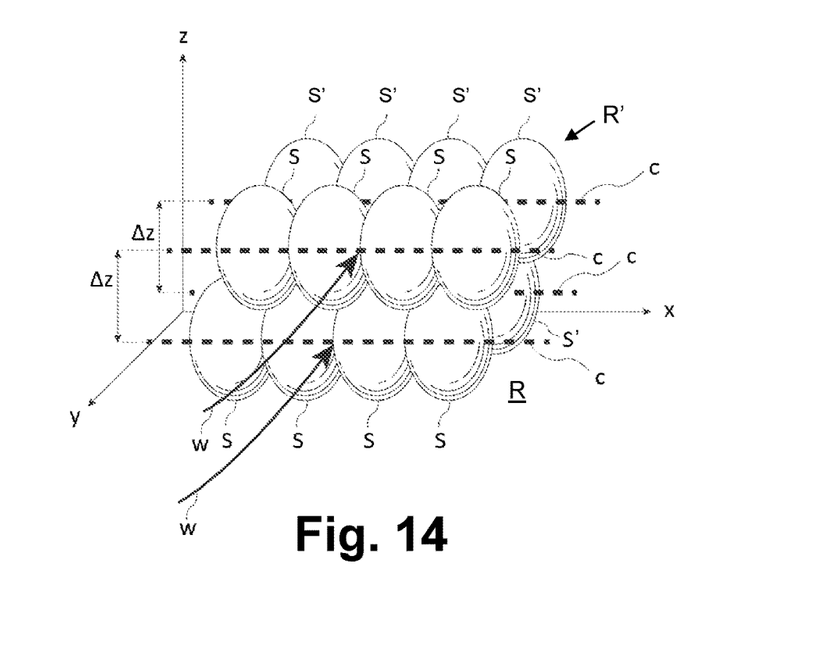
FIG. 14 shows a schematic three-dimensional view of a section of a void volume, created in the cornea by ablating cornea tissue inside the cornea with focal spots partially overlapping along scan lines, across neighbouring scan lines moved along the working line, and across superposed scan lines moved along the working line.

FIGS. 12 to 14 illustrate schematically partially overlapping focal spots S, S' with a spot diameter e typically in the range of 1 μm to 10 μm. It is pointed out here that the person skilled in the art will understand that a focal spot S refers to a laser interaction zone where tissue, here corneal tissue, is dissolved (ablated) to effect tissue cuts or volumetric tissue ablation. The extent of this zone or focal spot S, respectively, is in first approximation an ellipsoid with a length i (in z-direction or direction of projection p, respectively) and a diameter e (in the x/y-plane or normal to the z-direction or direction of projection p, respectively). Generally, the length i of a focal spot S is longer than its diameter e. Nevertheless, focusing optical modules with high numerical aperture may produce focal spots S with a more spherical shape where the length i corresponds to the diameter e.

FIGS. 12 to 14 illustrate schematically, the partial overlapping of the focal spots S moved along the scan line c. FIGS. 12 and 14 further illustrate schematically, the partial overlapping of the focal spots S of neighbouring scan lines c as indicated by focal spots S', depicted partially with dashed lines in FIG. 12 (e.g. neighbouring in x/y-plane). FIGS. 13 and 14, further illustrate schematically the partial overlapping of the focal spots S of superposed neighbouring scan lines c (e.g. superposed in z-direction). The person skilled in the art will further understand that, as an alternative to separating (corneal) tissue by way of dissolving/ablating the tissue in the separation area, using partially overlapping focal spots S, S' and generating a cut surface or an ablation volume in the separation area, (corneal) tissue may also be separated by means of expanding gas bubbles, using non-overlapping and/or spatially separated focal spots, whereby expanding gas bubbles cause separation through tearing and/or cleavage of tissue but do not dissolve or ablate tissue.

Figure 2:
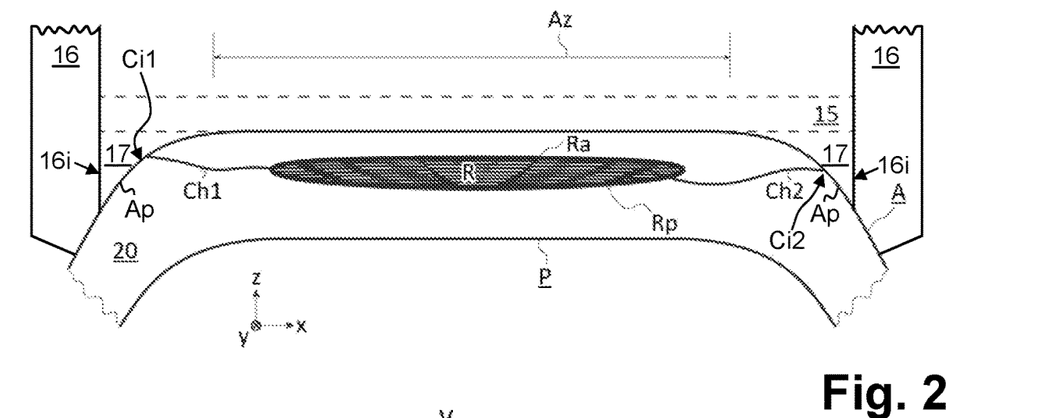
FIG. 2 shows a schematic cross-sectional view of a cornea in an applanated state with a void volume, created in shape of a lenticule for a desired myopic refractive correction of the cornea, and venting channels in the cornea, connected fluidically to the void volume.
Figure 11:
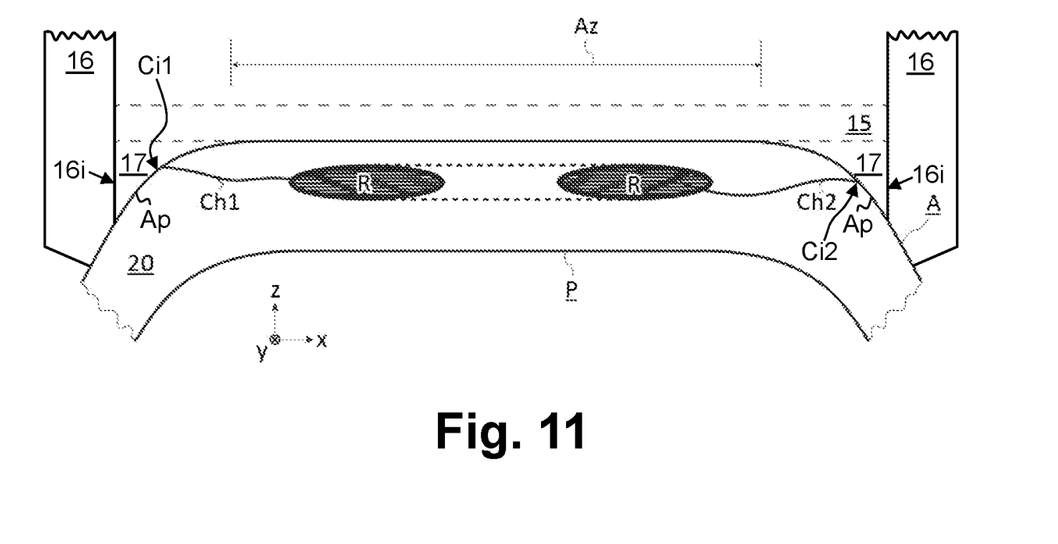
FIG. 11 shows a schematic cross-sectional view of a cornea in an applanated state with a void volume, created in shape of a ring for a desired hyperopic refractive correction of the cornea, and venting channels in the cornea, connected fluidically to the void volume.

As illustrated schematically in FIG. 14, the void volume R is a three-dimensional void volume R generated by the ophthalmological device 1 ablating cornea tissue inside the cornea 20 with partially overlapping focal spots S, whereby two or more focal spots S partially overlap in direction of each of the three dimensions x, y, z of the area inside the cornea 20 where the void volume R or of at least a section of the void volume R' is created. Accordingly, as shown in FIG. 14, each of the focal spots S partially overlaps in direction of each of the three dimensions x, y, z of the void volume R with at least one other focal spot S. As illustrated in FIGS. 2 and 11, the extent of the void volume R is determined by the anterior volume surface Ra of the void volume R, facing the exterior/anterior surface A of the cornea 20, and the posterior volume surface Rp of the void volume R, facing the posterior surface P of the cornea 20.

For creating the void volume R inside the cornea 20, the cornea tissue is processed with parameters of the pulsed laser beam B, including pulse energy, pulse overlap, pulse rate, pulse duration, and/or focal spot size of the pulsed laser beam B, which are set to dissolve the corneal tissue such as to perform volumetric ablation of the corneal tissue. More specifically, the parameters of the pulsed laser beam B are set to keep the energy density at or above the optical breakdown threshold for ablation (e.g. at approximately 0.5 $J/cm^2$ to 1 $J/cm^2$ energy density of a single pulse). The area inside the cornea 20 where the void region R is to created is processed with parameters of the pulsed laser beam B set to cause ablation of the corneal tissue.

As illustrated schematically in FIG. 1, the ophthalmological device 1 comprises a patient interface 18 for attaching the application head 14 or the focusing optical module 12, respectively, onto the eye 2. Depending on the embodiment, the patient interface 18 is connected to the application head 14 in a fixed or removable manner.

The patient interface 18 comprises a contact body 15 and one or more suction elements configured to fix the contact body 15 and thus the patient interface 18 to the cornea 20. For example, the one or more suction elements are arranged in a fastening ring 16, e.g. a vacuum-controlled suction ring, whereby the one or more suction elements are connected fluidically to a suction pump. The contact body 15, also referred to as applanation body, is at least partly light-transparent.

As illustrated in FIGS. 2 and 11, in the state where the patient interface 18 or the contact body 15, respectively, is fixed to the cornea 20, specifically to the exterior (anterior) surface A of the cornea 20, applanated is an applanation zone Az of the cornea 20, where the contact body 15 is in contact with the exterior (anterior) surface A of the cornea 20.

As is further illustrated in FIGS. 2 and 11, and also indicated in FIG. 1, in the state where the patient interface 18 or the applanation body 15, respectively, is fixed to the cornea 20, the fastening ring 16 and the applanation body 15 form an external venting chamber 17 with the peripheral area Ap of the exterior (anterior) surface A of the cornea 20 outside the applanation zone Az. The venting chamber 17 is defined by an interior wall 16i of the fastening ring 16, the surface of the applanation body 15 contacting the cornea 20, and the peripheral area Ap of the exterior (anterior) surface A of the cornea 20 outside the applanation zone Az.

The scanner system 13 is configured to move the focal spot S to target locations in the cornea 20 by guiding and directing the pulsed laser beam B and thus the focal spot S to target locations in the cornea 20.

Figure 3:
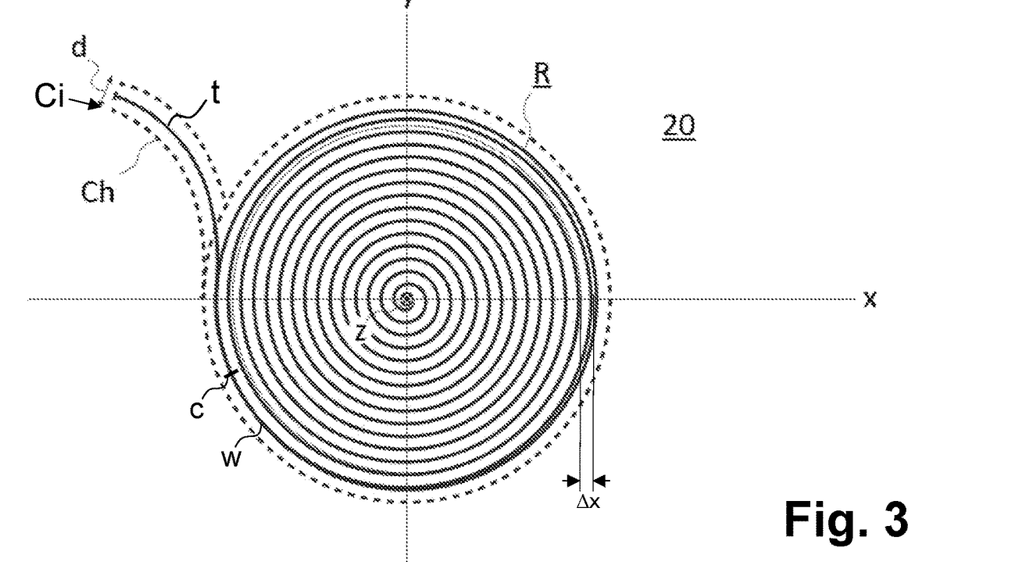
FIG. 3 shows a schematic top view of a cornea with a working line for cutting a venting channel in the cornea and, connected for a continuous movement of the focal spot, a spiral shaped working line for creating a void volume in the cornea.
Figure 4:
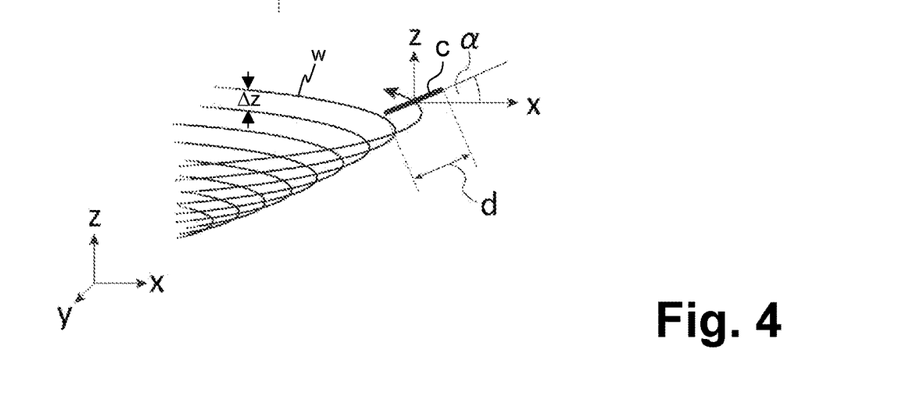
FIG. 4 shows a schematic three-dimensional view of a section of a spiral shaped working line for creating a void volume in the cornea.

The scanner system 13 comprises one or more scanner devices 131, also referred to as slow scanner device, configured to guide and direct the pulsed laser beam B and thus the focal spot S along a work line w, e.g. a spiral shaped work line, in a x/y-work-plane which is normal to a z-axis, whereby the z-axis is aligned with or essentially parallel to the projection axis p of the focusing optical module 12, as illustrated schematically in FIG. 1. Depending on the embodiment, the one or more scanner devices 131 comprise one or more actuators configured to move the focusing optical module 12 such that the focal spot S is moved along the work line w in the x/y-work-plane, and/or one or more deflection mirrors, each movable about one or two axes, configured to deflect the pulsed laser beam B and/or the laser pulses such that the focal spot S is moved along the work line w in the x/y-work-plane. To move the focal spot S along a work line w in the three-dimensional x/y/z-space, e.g. a spiral shaped work line w in the three-dimensional x/y/z-space, the one or more scanner devices 131 comprise one or more actuators configured to move the focusing optical module 12 or one or more of its optical lenses in z-direction, i.e. along the z-axis. FIG. 3 illustrates schematically in top view a spiral shaped working line w in the cornea 20. FIG. 4 shows a schematic three-dimensional view of a section of a spiral shaped working line w in the cornea 20.

The scanner system 13 comprises a further scanner device 132, also referred to as fast scanner device, configured to guide and direct the pulsed laser beam B and thus the focal spot S along a scan line c at a scanning speed that is comparatively faster than the scanning speed of the aforementioned slow scanner device 131. For example, the fast scanner device 132 comprises a polygon scanner. The fast scanner device 132 is configured to move the focal spot S, overlaid on the movement along the work line w, along a scan line c that runs through the work line w, at an angle to the work line w, as illustrated in FIGS. 3, 4, 12, and 14.

The scanner system 13 further comprises a divergence-modulator 133, also referred to as z-modulator, configured to move the focal spot S along the z-axis that is aligned with or essentially parallel to the projection axis p of the focusing optical module 12. The divergence modulator 133 is configured to dynamically change the divergence of the pulsed laser beam B. As illustrated schematically in FIGS. 4 and 12, the combined (synchronized) movement of the focal spot S by the aforementioned fast scanner device 132 and by the divergence-modulator 133 constitutes a movement of the focal spot S along a scan line c, which is bent and/or tilted with a tilting angle α from the x/y-plane. The electronic circuit 10 is configured to control the divergence-modulator 133 to adjust the tilting angle α of the scan line c with respect to the shape of the anterior volume surface Ra of the void volume R and/or the posterior volume surface Rp of the void volume R.

In an embodiment, the scanner system 13 further comprises an optional length modulator 130 configured to modulate the length of the scan line c. For example, the length modulator 130 comprises an adjustable shutter device arranged downstream of the fast scanner device 132. For example, the length d of the scan line c is adjusted by controlling the length modulator 130, e.g. the shutter device, to let through a set number of laser pulses from the fast scanner device 132 for producing a corresponding number of focal spots S. The electronic circuit 10 is configured to control the length modulator 130 to adjust the length d of the scan line c with respect to the shape of the anterior volume surface Ra of the void volume R or the posterior volume surface Rp of the void volume R.

As illustrated in FIG. 4, the synchronized combination of the movement of the focal spots S along the working line w in the x/y/z-space by the slow scanner device 131, with the overlaid movement of the focal spots S along the scan line c by the fast scanner device 132, and the tilting of the scan line c with a tilting angle α from the x/y-plane by the divergence-modulator 133, and optionally the adjustment of the length d of the scan line c by the length modulator 130, makes it possible not only to generate plane or curved cut surfaces inside the cornea 20, but also to perform with great flexibility volumetric ablation of corneal tissue. For example, volumetric ablation is achieved inside the cornea 20 by driving the scan line c overlaid on the work line w with a continuous increase Az in z-direction (per cycle) to generate superposed ablation layers with partially overlapping focal spots S along the scan line c (as illustrated in FIGS. 12 to 14), among neighbouring scan lines c (as illustrated in FIGS. 12 and 14), and among adjacent superposed ablation layers or scan lines, respectively (as illustrated in FIGS. 13 and 14).

Various further and more specific embodiments of the scanner system 13 are described by the applicant in patent applications US 2019/0015250, US 2019/0015251, and US 2019/0015253 which are hereby incorporated by reference.

In an embodiment, the ophthalmological device 1 further comprises a measurement system 19 configured to determine positional reference data of the cornea 20. Depending on the embodiment, the measurement system 19 comprises a video capturing system, an optical coherence tomography (OCT) system, and/or a structured light illumination system. Accordingly, the measurement data or positional reference data determined by the measurement system 19 includes video data, including top view data (comprising two-dimensional images), and/or OCT data of the cornea 20 (comprising three-dimensional tomography data). The measurement system 19 is configured to determine the positional reference data of the cornea 20 also in an applanated state of the cornea 20. The measurement system 19 is connected to and/or integrated with the electronic circuit 10, which is further configured to control the scanner system 13, using the positional reference data from the measurement system 19. For example, the measurement system 19 and/or the electronic circuit 10 are configured to determine as further positional reference data the peripheral area Ap of the exterior (anterior) surface A of the cornea 20 outside the applanation zone Az, using the measurement data or the positional reference data captured by the measurement system 19.

The electronic circuit 10 is configured to control the scanner system 13 to move the focal spot S inside the cornea 20 to generate the void volume R inside the cornea 20 for treatment of the cornea 20, such as for refractive correction of the cornea 20 or for inserting implants into the void volume R. More specifically, the electronic circuit 10 is configured to control the scanner system 13 to move the focal spot S inside the cornea 20 to generate the void volume R inside the cornea 20 by ablating the cornea tissue inside the void volume R. As describe above with reference to FIGS. 12-14, to create the void volume R the cornea tissue is ablated by moving the focal spot S inside the cornea 20 such that consecutive focal spots S partially overlap. The electronic circuit 10 is configured to control the scanner system 13 to move the focal spot S inside the cornea 20 to generate the void volume R inside the cornea 20 such that the cornea tissue is ablated with partially overlapping focal spots S in direction of each of the three dimensions x, y, z of at least a section R' of the area inside the cornea 20 where the void volume R is created.

To enable venting of gas, produced by generating the void volume R inside the cornea 20, the electronic circuit 10 is further configured to control the scanner system 13 to move the focal spot S inside the cornea 20 to cut in the cornea 20 one or more venting channels Ch, Ch1, Ch2 which connects fluidically the void volume R to an escape area. The venting channel(s) Ch, Ch1, Ch2 make(s) it possible to vent the gas from the void volume R to the escape area. Depending on the embodiment and/or configuration, the escape area is outside the cornea 20, i.e. exterior to the cornea 20, or inside the cornea 20, in a venting pocket P, described later in more detail. In the case where the escape area is exterior to the cornea 20, the venting channels Ch, Ch1, Ch2 connect fluidically the void volume R to an opening incision Ci, Ci1, Ci2 in the exterior (anterior) surface A of the cornea 20, as illustrated in FIGS. 1-3 and 5-11.

In an embodiment, the electronic circuit 10 is configured to control the scanner system 13 to move the focal spot S inside the cornea 20 to cut one or more venting pockets P inside the cornea 20.

In the following paragraphs, different arrangements and configurations of the void volume R, venting channels Ch, Ch1, Ch2, respective opening incisions Ci, Ci1, Ci2, and venting pockets P are described with reference to FIGS. 1-3 and 5-11. For the sake of clarity, it is pointed out here that the electronic circuit 10 is configured to control the scanner system 13 to move the focal spot S to generate the void volumes R, venting channels Ch, Ch1, Ch2, opening incisions Ci, Ci1, Ci2, and venting pockets P in the cornea 20 according to one or more of these configurations and combinations thereof, for example, as selected or selectable by an operator.

FIGS. 1 and 2 illustrate in cross-sectional view and FIGS. 3, 5, and 7-10 illustrate in top view examples of the void volume R created inside the cornea 20 in shape of a lenticule for a desired myopic refractive correction of the cornea 20. FIG. 11 illustrates in cross-sectional view and FIG. 6 illustrates in top view examples of the void volume R created inside the cornea 20 in shape of a ring for a desired hyperopic refractive correction of the cornea 20.

While FIGS. 1, 3, and 7-11 illustrate examples with one venting channel Ch, and FIGS. 2, 5, 6, and 11 illustrate examples with two venting channels Ch1, Ch2, it is pointed out for the sake of clarity, that the electronic circuit 10 may be configured to control the scanner system 13 to move the focal spot S to generate in all these examples one, two, or more venting channels Ch, Ch1, Ch2 in the cornea 20, for example, as selected or selectable by an operator.

The venting channels Ch, Ch1, Ch2 have a channel width d, d1, d2 defined by the width of the cut surface forming the venting channels Ch, Ch1, Ch2. As can be seen in FIGS. 3 and 5-10, the channel width d, d1, d2 is defined by the extension of the cut surfaces forming the venting channels Ch, Ch1, Ch2 in a horizontal x/y-working plane, for example. The channel width d, d1, d2 of the venting channels Ch, Ch1, Ch2 is far smaller than the length of the venting channels Ch, Ch1, Ch2, extending from the respective opening incisions Ci, Ci1, Ci2 to the void volume R. The relatively smaller channel widths d, d1, d2 or diameter of the cross-sectional profile of the venting channels Ch, Ch1, Ch2 is in the range of 0.1 mm to 0.8 mm, preferably in the range of 0.1 mm to 0.6 mm, whereas the length of the venting channels Ch, Ch1, Ch2 is in the range of 1 mm to 6 mm. In an embodiment, the venting channels Ch, Ch1, Ch2 are cut with a cross-shaped cross sectional profile of the venting channels Ch, Ch1, Ch2.

The electronic circuit 10 is further configured to control the scanner system 13 to move the focal spot S to cut in the cornea 20 the one or more venting channels Ch, Ch1, Ch2 from the outside to the inside of the cornea 20, i.e. commencing from the respective opening incision Ci, Ci1, Ci2 in the exterior (anterior) surface A of the cornea 20 through the cornea tissue to the area of the void volume R inside the cornea 20.

In an embodiment, the electronic circuit 10 is further configured to control the laser source 11 to set and use a comparatively higher energy level for cutting the opening incisions Ci, Coi1, Ci2 in the exterior (anterior) surface A of the cornea 20, and to reduce the energy level for cutting the venting channels Ch, Ch1, Ch2 beyond the opening incision Ci, Ci1, Ci2.

It should be pointed out that cutting the one or more venting channels Ch, Ch1, Ch2 from the outside to the inside of the cornea 20 produces gas which at least partially remains in the venting channels Ch, Ch1, Ch2 and keeps the venting channels Ch, Ch1, Ch2 open.

As is shown in FIGS. 2 and 11, the opening incisions Ci, Ci1, Ci2 of the venting channels Ch, Ch1, Ch2 are arranged in a peripheral area Ap of the exterior (anterior) surface A of the cornea 20, outside the applanation zone Az. Thus, the fluidic venting channels Ch, Ch1, Ch2 enable the venting of the gas, produced by generating the void volume R inside the cornea 20, through the respective opening incisions Ci, Ci1, Ci2 to the exterior of the cornea 20 outside the applanation zone Az. More specifically, the opening incisions Ci, Ci1, Ci2 of the venting channels Ch, Ch1, Ch2 are arranged in a peripheral area Ap of the exterior (anterior) surface A of the cornea 20 bordering onto the venting chamber 17. Thus, the fluidic venting channels Ch, Ch1, Ch2 enable the venting of the gas through the respective opening incisions Ci, Ci1, Ci2 into the venting chamber 17.

In an embodiment, the one or more suction elements of the fastening ring 16 apply—interruptedly or non-interruptedly—a partial vacuum to the venting chamber 17 and thereby further facilitate the venting of the gas, produced by generating the void volume R inside the cornea 20, through the fluidic venting channels Ch, Ch1, Ch2 and their respective opening incisions Ci, Ci1, Ci2 to the exterior of the cornea 20, outside the applanation zone Az, into the venting chamber 17.

In an embodiment, the electronic circuit 10 is configured to use the positional reference data from the measurement system 19 to control the scanner system 13 to move the focal spot S to cut in the cornea 20 the one or more venting channels Ch, Ch1, Ch2. For example, the electronic circuit 10 is configured to determine from the measurement data or the positional reference data, respectively, the peripheral area Ap of the exterior (anterior) surface A of the cornea 20, outside the applanation zone Az. More specifically, the electronic circuit 10 is configured to determine from the measurement data or the positional reference data, respectively, the peripheral area Ap of the exterior (anterior) surface A of the cornea 20, outside the applanation zone Az and bordering onto the venting chamber 17. Moreover, the electronic circuit 10 is configured to determine the location of the opening incisions Ci, Ci1, Ci2 inside the peripheral area Ap of the exterior (anterior) surface A of the cornea 20. In an embodiment, the electronic circuit 10 is configured to receive operator input, e.g. via a data entry element and/or a touchscreen, for selecting, moving, and/or positioning the location of the opening incisions Ci, Ci1, Ci2 within the peripheral area Ap of the exterior (anterior) surface A of the cornea 20.

Figure 5:
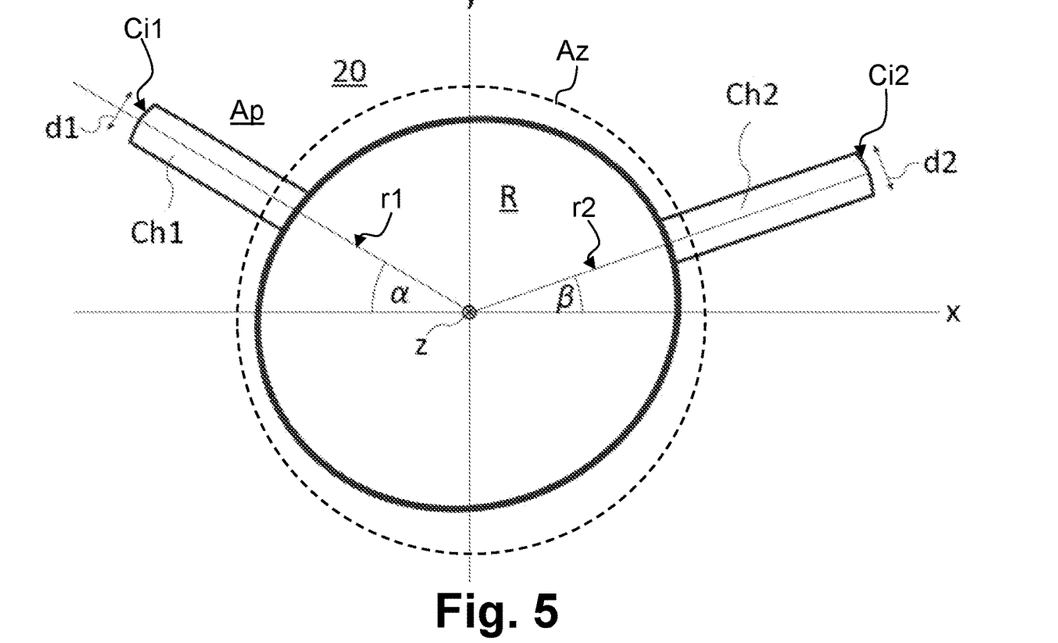
FIG. 5 shows a schematic top view of a cornea with a void volume, created in shape of a lenticule for a desired myopic refractive correction of the cornea, and venting channels in the cornea, connected fluidically to the void volume.
Figure 6:
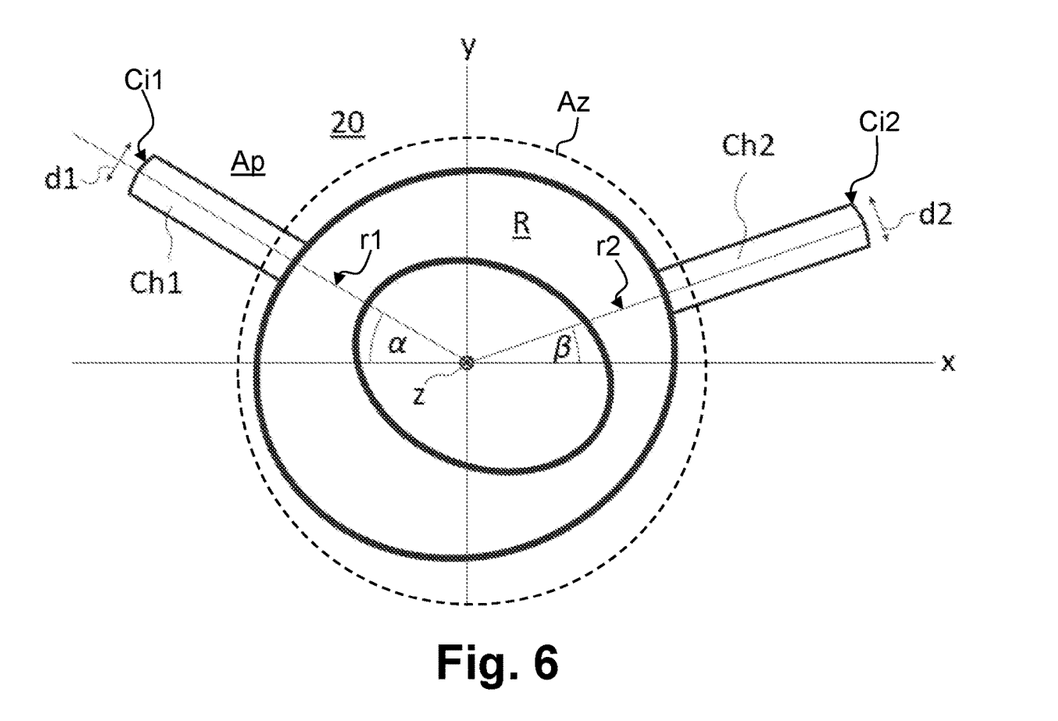
FIG. 6 shows a schematic top view of a cornea with a void volume, created in shape of a ring for a desired hyperopic refractive correction of the cornea, and venting channels in the cornea, connected fluidically to the void volume.

FIGS. 5 and 6 show scenarios where the electronic circuit 10 is configured to control the scanner system 13 to move the focal spot S along a radial trajectory r1, r2 directed towards a central axis z of the void volume R to cut one or more of the venting channels Ch1, Ch2 along the respective radial trajectory r1, r2. As illustrated in FIGS. 5 and 6, the radial trajectories r1, r2 are orientated at different angles α, β, e.g. with respect to a reference axis in the x/y-work plane, e.g. with respect to the x-axis, e.g. selected or set by the operator. As indicated in FIGS. 5 and 6, the venting channels Ch1, Ch2 may have different channel widths d1, d2, e.g. selected or set by the operator.

In an embodiment, the electronic circuit 10 is configured to control the scanner system 13 to move the focal spot S to cut the venting channels Ch, Ch1, Ch2 with a channel width which increases from the void volume R to the opening incision Ci, Ci1, Ci2, starting with a comparatively smaller channel width at the perimeter of the void volume R and increasing to a comparatively wider channel width d, d1, d2 at the opening incision Ci, Ci1, Ci2.

FIG. 3 shows a scenario where the electronic circuit 10 is configured to control the scanner system 13 to move the focal spot S along a working line w to cut the venting channel Ch and create the void volume R in a continuous movement of the focal spot S along the working line w. In the example illustrated in FIG. 3, the working line for creating the void volume R is a spiral shaped working line w. For example, the venting channel Ch is cut along a straight trajectory t that leads onto the spiral shaped working line w, or along a curved or tangential trajectory t that runs curved or tangentially onto the spiral shaped working line w.

FIGS. 7-10 illustrate different examples of various arrangements and configurations of the venting pocket(s) P inside the cornea 20.

Figure 7:
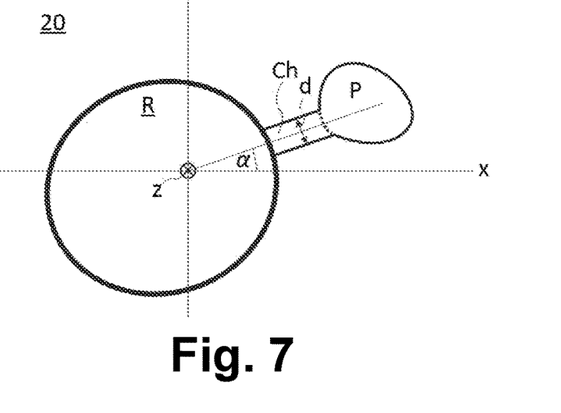
FIGS. 7-10 show schematic top views of a cornea with a void volume, a venting pocket, and a venting channel created in the cornea.

In the example of FIG. 7, the venting pocket P is cut as the escape area. The venting pocket P of FIG. 7 is fluidically connected to the void volume R by the venting channel Ch to enable the venting of the gas from the void volume R through the venting channel Ch to the venting pocket P that serves as the escape area.

Figure 8:
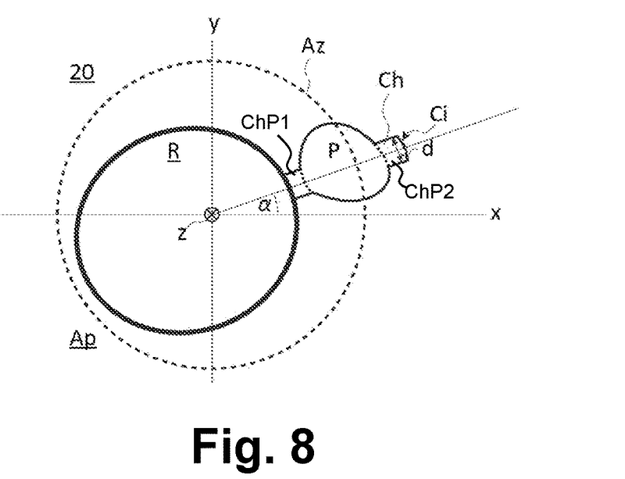

In the example of FIG. 8, the venting pocket P is cut as an intermediary escape area. The venting pocket P of FIG. 8 is fluidically connected to the void volume R, by a first part ChP1 of the venting channel Ch. Further, the venting pocket P of FIG. 8 is fluidically connected to the opening incision Ci in the exterior surface A of the cornea 20, by a second part ChP2 of the venting channel Ch. The arrangement and configuration illustrated in FIG. 8 enable the venting of the gas from the void volume R through the first part ChP1 of the venting channel Ch to the venting pocket P, and from the venting pocket P through the second part ChP2 of the venting channel Ch and through the opening incision Ci to the exterior to the cornea 20.

Figure 9:
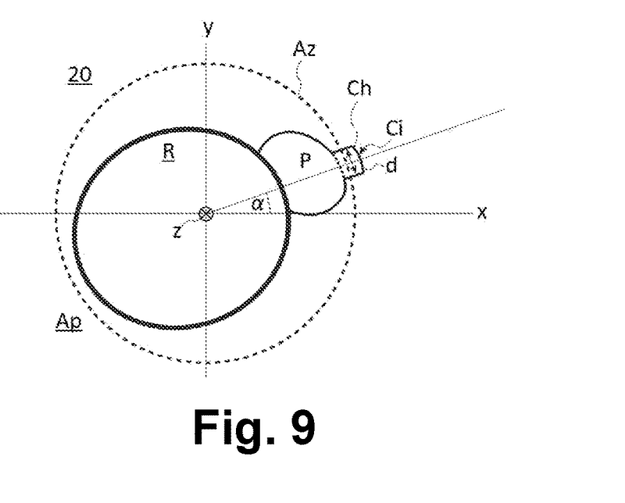

In the example of FIG. 9, the venting pocket P is cut adjacent and fluidically connected to the void volume R as an intermediary escape area. The venting pocket P of FIG. 9 is fluidically directly connected to the void volume R. Further, the venting pocket P of FIG. 9 is fluidically connected by the venting channel Ch to the opening incision Ci in the exterior surface A of the cornea 20. The arrangement and configuration illustrated in FIG. 9 enable the venting of the gas from the void volume R to the adjacent venting pocket P, and from the venting pocket P through the venting channel Ch and through the opening incision Ci to the exterior to the cornea 20.

Figure 10:
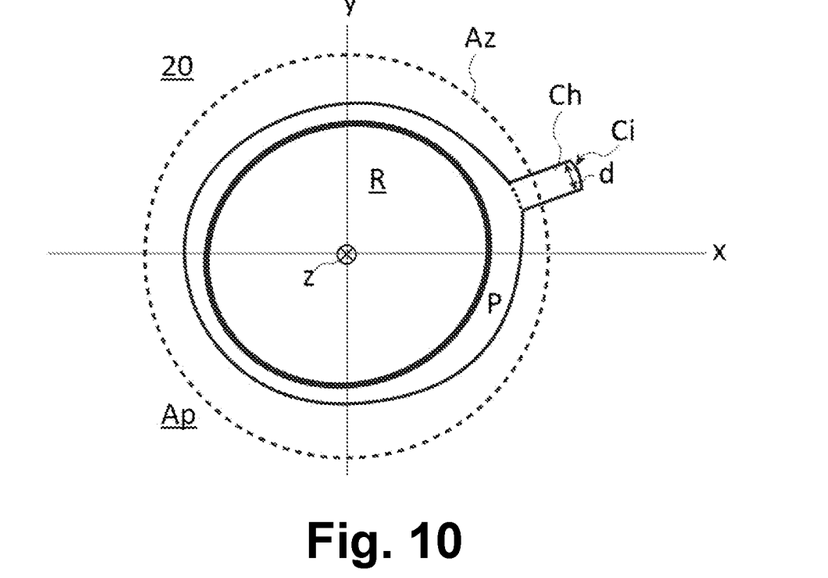

In the example of FIG. 10, the venting pocket P is cut adjacent to and surrounding the void volume R as an intermediary escape area. The venting pocket P of FIG. 10 is fluidically directly connected to the void volume R. Further, the venting pocket P of FIG. 10 is fluidically connected by the venting channel Ch to the opening incision Ci in the exterior surface A of the cornea 20. The arrangement and configuration illustrated in FIG. 10 enable the venting of the gas from the void volume R to the adjacent, surrounding venting pocket P, and from the venting pocket P through the venting channel Ch and through the opening incision Ci to the exterior to the cornea 20.

The invention claimed is:

1. An ophthalmological device for treatment of a cornea of an eye by generating a void volume inside the cornea, the ophthalmological device comprising:
    a laser source configured to generate a pulsed laser beam;
    a focusing optical module, comprising at least one optical lens, configured to make the pulsed laser beam converge onto a focal spot in the cornea;
    a scanner system configured to move the focal spot to target locations in the cornea; and
    an electronic circuit configured to control the scanner system to move the focal spot inside the cornea to generate the void volume by ablating cornea tissue inside the cornea with partially overlapping focal spots, whereby two or more focal spots partially overlap in direction of each of three dimensions of the void volume, such that each of the focal spots partially overlaps in direction of each of the three dimensions of the void volume with at least one other focal spot, and to move the focal spot inside the cornea to cut in the cornea a venting channel, the venting channel connecting fluidically the void volume to an escape area to enable venting of gas, produced by generating the void volume inside the cornea, from the void volume through the venting channel to the escape area.

2. The ophthalmological device of claim 1, wherein the electronic circuit is configured to control the scanner system to move the focal spot to cut an opening incision in an exterior surface of the cornea, and to cut the venting channel such that the venting channel connects fluidically the void volume to the opening incision to enable venting of the gas from the void volume through the opening incision to an escape area exterior to the cornea.

3. The ophthalmological device of claim 2, wherein the ophthalmological device further comprises a patient interface, the patient interface comprising a contact body, whereby in a state where the patient interface is fixed to the cornea the contact body is in contact with the exterior surface of the cornea in an applanation zone, and the electronic circuit is configured to control the scanner system to move the focal spot inside the cornea to cut in the cornea the venting channel with the opening incision located in a peripheral area of the exterior surface of the cornea outside the applanation zone.

4. The ophthalmological device of claim 3, wherein the patient interface further comprises one or more suction elements configured to fix the contact body to the cornea, and in the state where the patient interface is fixed to the cornea the one or more suction elements and the contact body form an external venting chamber with the peripheral area of the exterior surface of the cornea outside the applanation zone; and the electronic circuit is configured to control the scanner system to move the focal spot inside the cornea to cut in the cornea the venting channel with the opening incision inside the external venting chamber.

5. The ophthalmological device of claim 4, wherein the one or more suction elements are configured to apply a partial vacuum to the venting chamber and thereby further enable the venting of the gas.

6. The ophthalmological device of claim 1, wherein the electronic circuit is configured to control the scanner system to move the focal spot inside the cornea to ablate the cornea tissue inside the cornea to generate the void volume in shape of at least one of: a ring or a lenticule.

7. The ophthalmological device of claim 1, wherein the electronic circuit is configured to control the scanner system to move the focal spot inside the cornea to ablate the cornea tissue inside the cornea to generate the void volume such that the void volume has a rounded rim.

8. The ophthalmological device of claim 1, wherein the electronic circuit is configured to control the scanner system to move the focal spot inside the cornea to cut a venting pocket inside the cornea, whereby the venting pocket is cut in at least one of the following configurations: the venting pocket is cut as the escape area, fluidically connected to the void volume by the venting channel, to enable venting of the gas from the void volume through the venting channel to the venting pocket; the venting pocket is cut as an intermediary escape area, fluidically connected to the void volume by a first part of the venting channel and fluidically connected to an opening incision in an exterior surface of the cornea by a second part of the venting channel, to enable venting of the gas from the void volume through the first part of the venting channel to the venting pocket and from the venting pocket through the second part of the venting channel and through the opening incision to an escape area exterior to the cornea; the venting pocket is cut as an intermediary escape area, adjacent and fluidically connected to the void volume and fluidically connected to the opening incision in the exterior surface of the cornea by the venting channel, to enable venting of the gas from the void volume to the venting pocket and from the venting pocket through the venting channel and through the opening incision to the escape area exterior to the cornea; or the venting pocket is cut as an intermediary escape area, surrounding the void volume and fluidically connected to the void volume and fluidically connected to the opening incision in the exterior surface of the cornea by the venting channel, to enable venting of the gas from the void volume to the venting pocket and from the venting pocket through the venting channel and through the opening incision to the escape area exterior to the cornea.

9. The ophthalmological device of claim 1, wherein the scanner system comprises a first scanner device configured to move the focal spot with a first scanning speed to target locations along a working line, and a second scanner device configured to move the focal spot with a second scanning speed, comparatively faster than the first scanning speed, to target locations along a scan line which runs through the working line at an angle to the working line;
and the electronic circuit is configured to control the first scanner device to move the focal spot to target locations along a spiral shaped working line inside the cornea, and to control the second scanner device to move the focal spot to target locations along the scan line to ablate the cornea issue and generate the void volume.

10. The ophthalmological device of claim 9, wherein the scanner system comprises a z-modulator configured to adjust a location of the focal spot along an optical axis of the focusing optical module for tilting the scan line in direction of the optical axis; and the electronic circuit is configured to control the z-modulator to adjust a tilting angle of the scan line with respect to a shape of at least one of: an anterior volume surface of the void volume or a posterior volume surface of the void volume.

11. The ophthalmological device of claim 9, wherein the scanner system comprises a length modulator, comprising an adjustable shutter device, configured to modulate a length of the scan line; and the electronic circuit is configured to control the length modulator to adjust the length of the scan line with respect to a shape of at least one of: an anterior volume surface of the void volume or a posterior volume surface of the void volume.

12. The ophthalmological device of claim 1, wherein the electronic circuit is configured to control the scanner system to move the focal spot along a work line to cut the venting channel and at least one of an anterior volume surface of the void volume or a posterior volume surface of the void volume in a continuous movement of the focal spot along the work line.

13. The ophthalmological device of claim 1, wherein the ophthalmological device further comprises a measurement system configured to determine positional reference data of the cornea, and the electronic circuit is configured to control the scanner system to move the focal spot inside the cornea to cut the venting channel, using the positional reference data.

14. The ophthalmological device of claim 13, wherein the measurement system comprises at least one of a video capturing system or an optical coherence tomography system.

15. A computer program product comprising a non-transitory computer-readable medium having stored thereon computer program code for controlling a processor of an ophthalmological device which comprises a laser source configured to generate a pulsed laser beam, a focusing optical module, comprising at least one optical lens, configured to make the pulsed laser beam converge onto a focal spot in a cornea of an eye, and a scanner system configured to move the focal spot to target locations in the cornea, whereby the computer program code is configured to control the processor such that the processor:
    directs the scanner system to move the focal spot inside the cornea, to generate a void volume inside the cornea, by ablating cornea tissue inside the cornea with partially overlapping focal spots, whereby two or more focal spots partially overlap in direction of each of three dimensions of the void volume, such that each of the focal spots partially overlaps in direction of each of the three dimensions of the void volume with at least one other focal spot, and to move the focal spot inside the cornea to cut in the cornea a venting channel, the venting channel connecting fluidically the void volume to an escape area, to enable venting of gas, produced by generating the void volume inside the cornea, from the void volume through the venting channel to the escape area, whereby the escape area is exterior to the cornea or inside the cornea.

16. The computer program product of claim 15, having further computer program code stored on the computer-readable medium and configured to control the processor such that the processor controls the scanner system to move the focal spot along a work line to cut the venting channel and at least one of an anterior volume surface of the void volume or a posterior volume surface of the void volume in a continuous movement of the focal spot along the work line.

17. A method comprising:
    generating, by a laser source, a pulsed laser beam;
    making, by a focusing optical module comprising at least one optical lens, the pulsed laser beam converge onto a focal spot in a cornea of an eye;
    moving, by a scanner system, the focal spot to target locations in the cornea; and
    controlling, by an electronic circuit, the scanner system to move the focal spot inside the cornea to generate a void volume by ablating cornea tissue inside the cornea with partially overlapping focal spots, whereby two or more focal spots partially overlap in direction of each of three dimensions of the void volume, such that each of the focal spots partially overlaps in direction of each of the three dimensions of the void volume with at least one other focal spot, and to move the focal spot inside the cornea to cut in the cornea a venting channel, the venting channel connecting fluidically the void volume to an escape area to enable venting of gas, produced by generating the void volume inside the cornea, from the void volume through the venting channel to the escape area.

18. The method of claim 17, wherein the electronic circuit is configured to control the scanner system to move the focal spot to cut an opening incision in an exterior surface of the cornea, and to cut the venting channel such that the venting channel connects fluidically the void volume to the opening incision to enable venting of the gas from the void volume through the opening incision to an escape area exterior to the cornea.

19. The method of claim 17, wherein the electronic circuit is configured to control the scanner system to move the focal spot inside the cornea to ablate the cornea tissue inside the cornea to generate the void volume in shape of at least one of: a ring or a lenticule.

20. An ophthalmological device for treatment of a cornea of an eye by generating a void volume inside the cornea, the ophthalmological device comprising:

a laser source configured to generate a pulsed laser beam;

a focusing optical module, comprising at least one optical lens, configured to make the pulsed laser beam converge onto a focal spot in the cornea;

a scanner system configured to move the focal spot to target locations in the cornea; and an electronic circuit configured to control the scanner system to move the focal spot inside the cornea to generate the void volume by ablating cornea tissue inside the cornea with partially overlapping focal spots, whereby two or more focal spots partially overlap in direction of each of three dimensions of the void volume, and to move the focal spot inside the cornea to cut in the cornea a venting channel, the venting channel connecting fluidically the void volume to an escape area to enable venting of gas, produced by generating the void volume inside the cornea, from the void volume through the venting channel to the escape area, wherein the scanner system comprises a first scanner device configured to move the focal spot with a first scanning speed to target locations along a working line, and a second scanner device configured to move the focal spot with a second scanning speed, comparatively faster than the first scanning speed, to target locations along a scan line which runs through the working line at an angle to the working line; and the electronic circuit is configured to control the first scanner device to move the focal spot to target locations along a spiral shaped working line inside the cornea, and to control the second scanner device to move the focal spot to target locations along the scan line to ablate the cornea issue and generate the void volume.

* * * * *